(12) United States Patent
Nakamori et al.

(10) Patent No.: US 12,716,063 B2
(45) Date of Patent: Aug. 25, 2026

(54) BIOLOGICAL MATERIAL EXTRACTION CARRIER AND BIOLOGICAL MATERIAL EXTRACTION METHOD

(71) Applicant: SEIKO EPSON CORPORATION, Tokyo (JP)

(72) Inventors: Michio Nakamori, Matsumoto (JP); Masato Hanamura, Shiojiri (JP)

(73) Assignee: SEIKO EPSON CORPORATION (JP)

( * ) Notice: Subject to any disclaimer, the term of this patent is extended or adjusted under 35 U.S.C. 154(b) by 678 days.

(21) Appl. No.: 18/189,506

(22) Filed: Mar. 24, 2023

(65) Prior Publication Data

US 2023/0303997 A1 Sep. 28, 2023

(30) Foreign Application Priority Data

Mar. 25, 2022 (JP) ................................ 2022-049465

(51) Int. Cl.

| | |
|---|---|
| ***C12N 15/00*** | (2006.01) |
| ***B01D 15/20*** | (2006.01) |
| ***B01D 15/38*** | (2006.01) |
| ***B01D 15/42*** | (2006.01) |
| ***B03C 1/01*** | (2006.01) |
| ***B03C 1/02*** | (2006.01) |
| ***C12N 15/10*** | (2006.01) |

(52) U.S. Cl.

CPC ....... *C12N 15/1013* (2013.01); *B01D 15/206* (2013.01); *B01D 15/3885* (2013.01); *B01D 15/424* (2013.01); *B03C 1/01* (2013.01); *B03C 1/02* (2013.01); *B03C 2201/18* (2013.01); *B03C 2201/20* (2013.01)

(58) Field of Classification Search

CPC ............. C12N 15/1013; B01D 15/206; B01D 15/3885; B01D 15/424; B03C 1/01; B03C 1/02; B03C 2201/18; B03C 2201/20

USPC ......................................................... 502/405

See application file for complete search history.

(56) References Cited

U.S. PATENT DOCUMENTS

| | | | |
|---|---|---|---|
| 2017/0073667 | A1 | 3/2017 | Ohashi et al. |
| 2017/0342400 | A1 | 11/2017 | Burr et al. |

FOREIGN PATENT DOCUMENTS

| | | | | |
|---|---|---|---|---|
| JP | 11262387 | A | * | 9/1999 |
| JP | H11-262387 | A | | 9/1999 |
| JP | 2007-224323 | A | | 9/2007 |
| JP | 4775713 | B2 | * | 9/2011 |
| JP | 2013209693 | A | * | 10/2013 |
| WO | 2015-136689 | A1 | | 9/2015 |

* cited by examiner

*Primary Examiner* — James E Mcdonough

(74) *Attorney, Agent, or Firm* — Harness, Dickey & Pierce, P.L.C.

(57) ABSTRACT

A biological material extraction carrier includes a magnetic bead including a magnetic metal powder and a first coating layer that coats a particle surface of the magnetic metal powder and that is made of a first oxide material, and an oxide powder, in which a particle surface is made of a second oxide material, and an average particle diameter is smaller than that of the magnetic bead. Further, the average particle diameter of the magnetic bead is preferably 0.5 μm or more and 50 μm or less.

6 Claims, 4 Drawing Sheets

BIOLOGICAL MATERIAL EXTRACTION CARRIER AND BIOLOGICAL MATERIAL EXTRACTION METHOD

The present application is based on, and claims priority from JP Application Serial Number 2022-049465, filed Mar. 25, 2022, the disclosure of which is hereby incorporated by reference herein in its entirety.

BACKGROUND

1. Technical Field

The present disclosure relates to a biological material extraction carrier and a biological material extraction method.

2. Related Art

In recent years, the demand for testing a biological material has increased in diagnoses in the medical field or in the field of life sciences. In a biological material testing method, the PCR (Polymerase chain reaction) method is a method in which a nucleic acid such as DNA or RNA is extracted and the nucleic acid is specifically amplified and detected. In the process of testing such a biological material, first, it is necessary to extract a material to be tested from a specimen. In the extraction of this biological material, a magnetic separation method using magnetic beads is widely used. In the magnetic separation method, magnetic beads having a function capable of supporting a biological material to be extracted are used, and the biological material is extracted by applying a magnetic field thereto. Specifically, after dispersing magnetic beads having a surface capable of supporting a material to be tested in a dispersion medium, the obtained dispersion is placed in a magnetic field generator such as a magnetic stand, and the application of a magnetic field is repeated several times. Thereby, the material to be tested is extracted. such a magnetic separation method is a method of separating and recovering magnetic beads by a magnetic force, and therefore enables a rapid separation operation.

In addition, a similar magnetic separation method is used not only in the extraction in the PCR method, but also in the field of protein purification, exosome or cell separation, extraction, or the like.

For example, JP-A-11-262387 discloses a nucleic acid-binding magnetic carrier, which is a magnetic silica particle containing a superparamagnetic metal oxide, wherein the magnetic silica particle has an external surface area of at least 50 $m^2/g$. Such a nucleic acid-binding magnetic carrier contains a superparamagnetic metal oxide, and therefore, it is possible to repeat a cycle of magnetic separation and redispersion. In addition, since the external surface area is large, a nucleic acid can be efficiently recovered from a biological sample.

When the surface area of the magnetic silica particle is increased, the recovery amount of a nucleic acid can be increased, but it is necessary to decrease the particle diameter of the magnetic silica particle. In that case, there is a problem that the saturation magnetization of the magnetic silica particle decreases and the separation speed in magnetic separation decreases. Further, when the particle diameter of the magnetic silica particle is decreased, the magnetic separation performance decreases, and therefore, there is also a problem that the amount of a nucleic acid that can be recovered decreases.

On the other hand, when the particle diameter of the magnetic silica particle is increased, the saturation magnetization of the magnetic silica particle increases, and therefore, the separation speed and magnetic separation performance in magnetic separation are improved. However, the surface area of the magnetic silica particle decreases, and therefore, the amount of a nucleic acid that can be recovered decreases. In particular, when the molecular weight of a nucleic acid is small, this tendency is remarkable.

SUMMARY

Therefore, an object of the present disclosure is to increase the amount of a biological material that can be recovered while increasing the separation speed in magnetic separation.

A biological material extraction carrier according to an application example of the present disclosure includes:

- a magnetic bead including a magnetic metal powder and a first coating layer that coats a particle surface of the magnetic metal powder and that is made of a first oxide material; and
- an oxide powder, in which a particle surface is made of a second oxide material, and an average particle diameter is smaller than that of the magnetic bead.

A biological material extraction method according to an application example of the present disclosure includes:

- an adsorption step in which a biological material, an adsorption liquid, and the biological material extraction carrier according to an aspect of the present disclosure are placed in a container and mixed, thereby associating the magnetic bead with the oxide powder through the biological material and obtaining an associated body; and
- an elution step in which the biological material extraction carrier that forms the associated body is brought into contact with an elution liquid to elute the biological material in the elution liquid, and thereafter, the elution liquid containing the biological material is discharged from the container in a state where the biological material extraction carrier is fixed to an inner wall of the container by applying an external magnetic field thereto.

BRIEF DESCRIPTION OF THE DRAWINGS

FIG. 7 is a process chart for illustrating a biological material extraction method according to an embodiment.

DESCRIPTION OF EXEMPLARY EMBODIMENTS

Hereinafter, preferred embodiments of a biological material extraction carrier and a biological material extraction method according to the present disclosure will be described in detail with reference to the accompanying drawings.

1. Biological Material Extraction Carrier

A biological material extraction carrier according to an embodiment is a particle group that includes a magnetic bead and an oxide powder, adsorbs a biological material, and is used for magnetic separation. The magnetic separation is a method in which an external magnetic field is applied to a container containing a solid phase including a magnetic bead and an oxide powder and a liquid phase including a dispersion medium to magnetically attract the solid phase, thereby separating the solid phase from the liquid phase.

The biological material refers to, for example, a nucleic acid such as DNA or RNA, a protein, a saccharide, various cells such as cancer cells, or a material such as a peptide, a bacterium, or a virus. The nucleic acid may exist, for example, in a state of being contained in a biological sample such as a cell or a biological tissue, a virus, a bacterium, or the like. The biological material extraction carrier according to the embodiment is used for purification of such a biological material using magnetic separation of the extraction carrier and the liquid when the biological material is extracted through respective steps of dissolution/adsorption, separation, washing, and elution.

Figure 1:
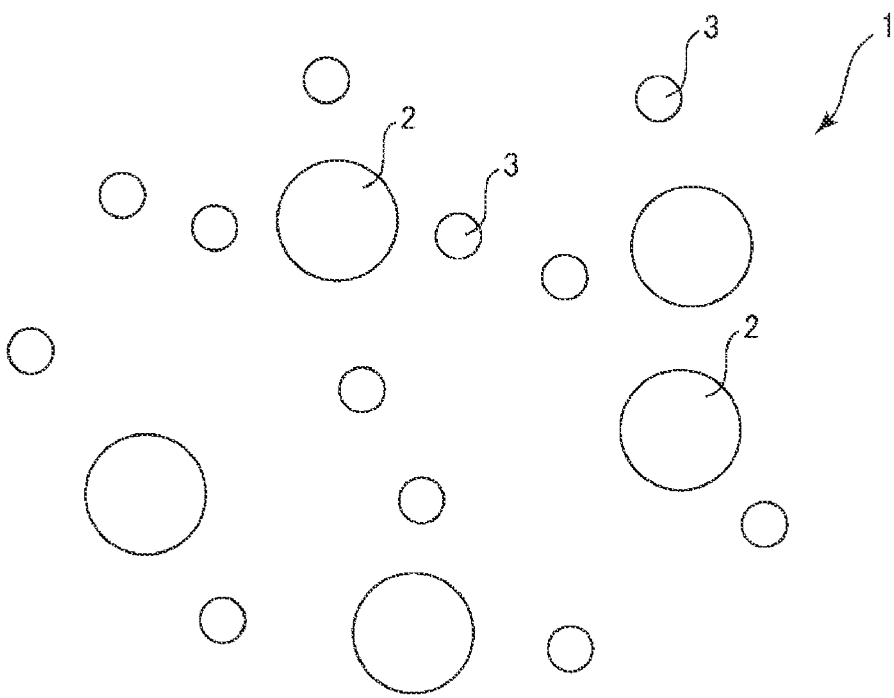
FIG. 1 is a schematic view showing a biological material extraction carrier according to an embodiment.
Figure 2:
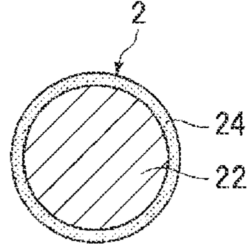
FIG. 2 is a cross-sectional view showing a magnetic bead in FIG. 1.

FIG. 1 is a schematic view showing a biological material extraction carrier 1 according to an embodiment. FIG. 2 is a cross-sectional view showing a magnetic bead 2 in FIG. 1.

The biological material extraction carrier 1 shown in FIG. 1 includes the magnetic bead 2 and an oxide powder 3.

As shown in FIG. 2, the magnetic bead 2 is a particle including a magnetic metal powder 22 and a coating layer 24 (first coating layer) that coats the particle surface of the magnetic metal powder 22. The magnetic metal powder 22 has magnetism, and therefore, when an external magnetic field acts on the magnetic bead 2, a magnetic attractive force is generated, and it is captured by the external magnetic field. The coating layer 24 is made of a first oxide material, which will be described in detail later, and has a function of adsorbing a biological material.

The oxide powder 3 has a particle surface made of a second oxide material, which will be described in detail later, and has a function of adsorbing a biological material. Further, an average particle diameter of the oxide powder 3 is smaller than that of the magnetic bead 2. Therefore, when a biological material is adsorbed to both the magnetic bead 2 and the oxide powder 3, a plurality of particles of the oxide powder 3 are associated with one magnetic bead 2 through the biological material.

Figures 3, 4:
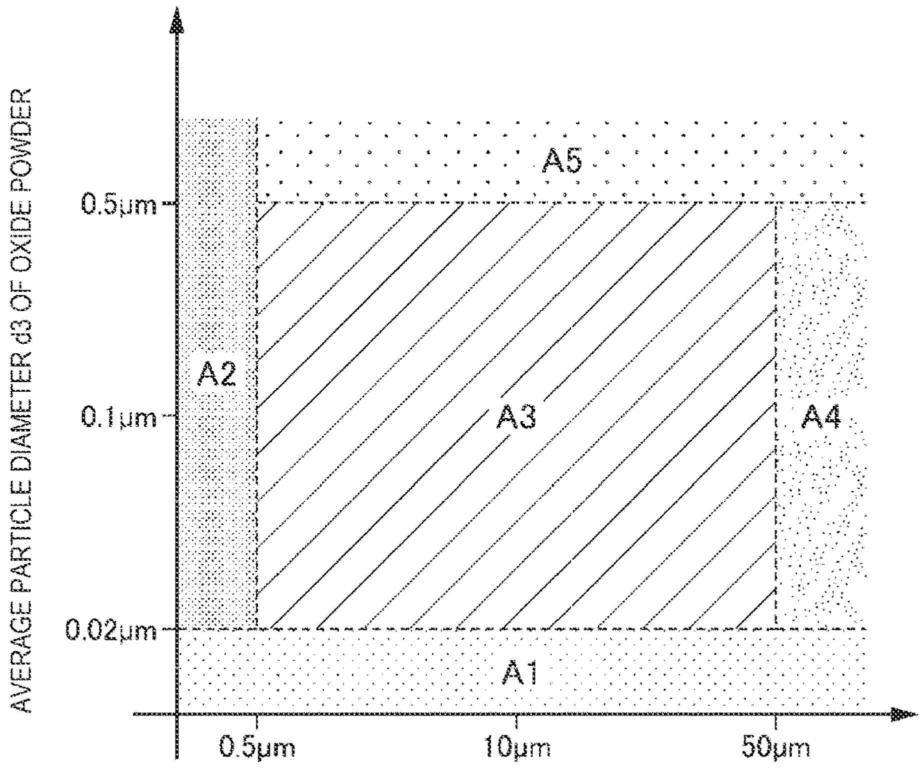
FIG. 3 is a schematic view showing an example in which an associated body resulting from association of one magnetic bead with a plurality of particles of an oxide powder through a nucleic acid is formed in a liquid containing the nucleic acid.
FIG. 4 is a graph showing a relationship between the average particle diameter d2 of a magnetic bead and the average particle diameter d3 of an oxide powder.

FIG. 3 is a schematic view showing an example in which an associated body 4 resulting from association of one magnetic bead 2 with a plurality of particles of the oxide powder 3 through a nucleic acid 9 is formed in a liquid containing the nucleic acid 9. In FIG. 3, the nucleic acid 9 is illustrated as an example of the biological material, but the biological material is not limited to the nucleic acid 9. Further, in the associated body 4, a plurality of magnetic beads 2 may be included.

The associated body 4 shown in FIG. 3 contains a plurality of particles of the oxide powder 3, and therefore has a large specific surface area and adsorbs a large amount of the nucleic acid 9. On the other hand, since the associated body 4 shown in FIG. 3 contains the magnetic bead 2, even if it contains the oxide powder 3 having no magnetism, it can be captured by an external magnetic field. Then, in the associated body 4, a plurality of particles of the oxide powder 3 smaller than the magnetic bead 2 are contained, and therefore, even if the size of the magnetic bead 2 is increased, a decrease in the specific surface area can be suppressed. Therefore, the magnetic bead 2 having a large particle diameter and a high saturation magnetization can be used, and the magnetic attractive force of the associated body 4 can be increased. As a result, according to the biological material extraction carrier 1, the nucleic acid 9 can be extracted and recovered in high yield while increasing the separation speed in magnetic separation. In addition, the oxide powder 3 enters a gap between the magnetic beads 2 so as to reduce the gap, and therefore, the amount of a liquid remaining in the gap (residual liquid amount) after magnetic separation can be reduced.

1.1. Magnetic Bead

The average particle diameter d2 of the magnetic bead 2 is set to preferably 0.5 μm or more and 50 μm or less, more preferably 1 μm or more and 30 μm or less, and even more preferably 2 μm or more and 20 μm or less. When the average particle diameter d2 of the magnetic bead 2 is within the above range, the specific surface area of the magnetic bead 2 can be sufficiently increased, and the mass and saturation magnetization of the magnetic bead 2 are suitable for magnetic separation. In other words, the magnetic bead 2 that has a specific surface area capable of adsorbing a sufficient amount of a biological material and that exhibits a magnetic attractive force with excellent moving speed in a magnetic field is obtained. Further, aggregation of the magnetic beads 2 can be suppressed, and redispersibility can be enhanced. In addition, the amount of a liquid remaining in the gap between the magnetic beads 2 (residual liquid amount) can be reduced.

When the average particle diameter d2 of the magnetic bead 2 is less than the above lower limit, the magnetization value of the magnetic bead 2 becomes small, and also, the beads tend to aggregate, and as a result, the extraction efficiency of the biological material may decrease. In addition, the moving speed of the magnetic bead 2 in magnetic separation may decrease, and the time required for magnetic separation may increase. On the other hand, when the average particle diameter d2 of the magnetic bead 2 exceeds the above upper limit, the specific surface area of the magnetic bead 2 becomes small, and therefore, a sufficient amount of the biological material cannot be adsorbed, and the extraction amount of the biological material may decrease. Further, the magnetic bead 2 tends to precipitate, and the magnetic bead 2 that can contribute to the extraction of the biological material decreases, and the extraction efficiency of the biological material may decrease. In addition, the residual liquid amount may increase.

The average particle diameter d2 of the magnetic bead 2 can be determined from an integrated distribution curve obtained from a volume-based particle size distribution measured by a laser diffraction/dispersion method. Specifically, the average particle diameter d2 of the magnetic bead 2 is a particle diameter D50 (median diameter) at which the cumulative value from the smaller diameter side in the integrated distribution curve is 50%. Examples of an apparatus for measuring the particle size distribution by a laser diffraction/dispersion method include Microtrac MT3000II series manufactured by MicrotracBEL Corp. When the measurement by the laser diffraction/dispersion method is difficult, a technique such as an image analysis may be used.

Further, when the average thickness of the coating layer 24 is represented by t2 and the average particle diameter of the magnetic bead 2 is represented by d2, the ratio of t2 to d2: t2/d2 is preferably 0.0001 or more and 0.05 or less, and more preferably 0.001 or more and 0.01 or less. When t2/d2 is less than the above lower limit, the ratio of the thickness of the coating layer 24 to the size of the magnetic metal powder 22 becomes too small, and therefore, when the magnetic beads 2 collide with each other or the magnetic bead 2 collides with the inner wall of the container or the like, the coating layer 24 may be broken or peeled off. Therefore, the amount of the biological material that is adsorbed to the surface of the coating layer 24 and extracted is reduced, and the extraction efficiency may decrease. In addition, fragments of the peeled coating layer 24 or the magnetic metal powder 22 are present in the dispersion, and may be simultaneously mixed as contaminants (contamination) when the biological material is taken out. Further, when the magnetic metal powder 22 is exposed by breaking or peeling the coating layer 24 and comes into contact with an acidic solution or the like, iron ions and the like may be eluted, resulting in a decrease in the extraction efficiency of the biological material. On the other hand, when t2/d2 exceeds the above upper limit, the volume ratio of the coating layer 24 to the entire volume of the magnetic bead 2 becomes large, and magnetization per volume of the magnetic bead 2 may decrease. Due to this, the moving speed when an external magnetic field acts on the magnetic bead 2 may decrease, and the time required for magnetic separation may increase.

The thickness of the coating layer 24 can be measured, for example, from a cross-sectional observation image of the magnetic bead 2 by a transmission electron microscope, a scanning electron microscope, or the like. Also, the average thickness t2 of the coating layer 24 can be calculated by obtaining a plurality of observation images and averaging the measured values from image processing or the like. For example, the average thickness t2 is a value obtained by measuring the thickness of the coating layer 24 at 5 or more locations for one magnetic bead 2, calculating the average value, and then averaging the average values for 10 or more magnetic beads 2.

In addition, in ESCA (Electron Spectroscopy for Chemical Analysis) or the like, the thickness of the coating layer can also be measured by performing a composition analysis in the depth direction using ion etching.

The saturation magnetization of the magnetic bead 2 is preferably 50 emu/g or more, and more preferably 100 emu/g or more. The saturation magnetization is a value of magnetization exhibited by a magnetic material when a sufficiently large magnetic field is applied from the outside. The higher the saturation magnetization of the magnetic bead 2 is, the more fully the function as a magnetic material can be exhibited. Specifically, since the moving speed of the magnetic bead 2 in the magnetic field can be improved, the time required for magnetic separation can be shortened. Further, the saturation magnetization of the magnetic bead 2 affects the adsorption force when it is fixed by an external magnetic field. When the saturation magnetization is within the above range, a sufficiently high adsorption force is obtained, and therefore, when the magnetically separated liquid is discharged, the magnetic bead 2 can be prevented from being discharged together with the liquid. This can suppress a decrease in the yield of the biological material due to a decrease in the magnetic bead 2.

The upper limit of the saturation magnetization of the magnetic bead 2 is not particularly limited, but is preferably set to 220 emu/g or less from the viewpoint of ease of selection of a material suitable for the balance between performance and cost.

The saturation magnetization of the magnetic bead 2 can be measured by a vibrating sample magnetometer (VSM) or the like. Examples of the vibrating sample magnetometer include TM-VSM1230-MHHL manufactured by Tamakawa Co., Ltd. The maximum applied magnetic field when measuring the saturation magnetization is set to, for example, 0.5 T or more.

The coercive force Hc of the magnetic bead 2 is preferably 1500 A/m or less, more preferably 800 A/m or less, and even more preferably 200 A/m or less. The coercive force Hc refers to a value of an external magnetic field in the opposite direction necessary for returning a magnetized magnetic body to an unmagnetized state. That is, the coercive force Hc means a resistance force to an external magnetic field. As the coercive force Hc of the magnetic bead 2 is smaller, the magnetic beads 2 are difficult to aggregate even when changing from a state where a magnetic field is applied to a state where a magnetic field is not applied, and the magnetic beads 2 can be uniformly dispersed in the dispersion. In addition, even when the application of a magnetic field is repeatedly switched, the smaller the coercive force Hc is, the better the redispersibility of the magnetic beads 2 is, and therefore, the aggregation of the magnetic beads 2 can be further suppressed. The lower limit of the coercive force Hc of the magnetic bead 2 is not particularly limited, but is preferably 1 A/m or more from the viewpoint of ease of selection of a material suitable for the balance between performance and cost.

The coercive force Hc of the magnetic bead 2 can be measured by a vibrating sample magnetometer or the like. Examples of the vibrating sample magnetometer include TM-VSM1230-MHHL manufactured by Tamakawa Co., Ltd. The maximum applied magnetic field when measuring the coercive force Hc is set to, for example, 15 kOe.

The relative magnetic permeability of the magnetic bead 2 is preferably 5 or more. When the relative magnetic permeability of the magnetic bead 2 is less than the above lower limit, the moving speed of the magnetic bead 2 may decrease and the time required for magnetic separation may increase. The upper limit of the relative magnetic permeability of the magnetic bead 2 is not particularly limited, but since the magnetic bead 2 is in a powder form, the relative magnetic permeability often takes a value of substantially 100 or less due to the effect of a demagnetizing field.

The magnetic bead 2 as used herein refers to a particle group or one particle forming the group.

1.1.1. Magnetic Metal Powder

The magnetic metal powder 22 is particles having magnetism, and preferably contains at least one of Fe, Co, and Ni as a constituent element. In particular, from the viewpoint of obtaining a high saturation magnetization, the composition of the magnetic metal powder 22 is preferably an alloy containing Fe as a main component (Fe-based alloy). Specifically, the atomic number ratio of Fe is set to more preferably 50% or more, and even more preferably 70% or more. Further, the composition of the magnetic metal powder 22 may be an alloy (Fe-based alloy) containing Fe as a main component, and for example, an Fe—Co-based alloy, an Fe—Ni-based alloy, an Fe—Co—Ni-based alloy, a compound containing Fe, Co, and Ni, and the like can be exemplified. Further, from the viewpoint of obtaining a high magnetization, as the magnetic metal powder 22, a carbonyl iron powder made of substantially 100 mass % of Fe, an Fe—Si-based alloy powder, an Fe—Si—Cr-based alloy powder, or the like is preferably used. Such an Fe-based alloy can realize the magnetic metal powder 22 that exhibits a high saturation magnetization and a high magnetic permeability even if the particle diameter is small. This can realize the magnetic bead 2 that has a high moving speed under the action of an external magnetic field and has a large magnetic adsorption force when it is captured by an external magnetic field. As a result, the time required for magnetic separation can be shortened, and the magnetic bead 2 itself can be prevented from mixing in the elution liquid and becoming a contaminant.

The Fe-based alloy can contain one or more types selected from the group consisting of Cr, Nb, Cu, Al, Mn, Mo, Si, Sn, B, C, P, Ti, and Zr according to the target properties in addition to an element exhibiting ferromagnetism by itself such as Co or Ni as described above. Si is a main constituent element in an alloy powder, but is also an element that promotes amorphization.

The Fe-based alloy may contain impurities as long as the effect of the magnetic metal powder 22 is not impaired. Impurities in the present embodiment are elements that are unintentionally mixed in a raw material of the magnetic metal powder 22 or when producing the magnetic bead 2. The impurities are not particularly limited, but examples thereof include O, N, S, Na, Mg, and K.

As an example of the Fe-based alloy, an alloy in which the Si content is preferably 1.0 at % or more and 30.0 at % or less, more preferably 1.5 at % or more and 13.0 at % or less, and even more preferably 2.0 at % or more and 7.0 at % or less is exemplified. Such an alloy has a high magnetic permeability and therefore tends to have a high saturation magnetization.

The Fe-based alloy may contain at least one of B (boron) with a content of 5.0 at % or more and 16.0 at % or less and C (carbon) with a content of 0.5 at % or more and 5.0 at % or less. These are elements that promote amorphization and contribute to the formation of a stable amorphous structure or nanocrystalline structure in the magnetic metal powder 22.

Further, the Fe-based alloy preferably contains Cr (chromium) with a content of 1.0 at % or more and 8.0 at % or less. According to this, the corrosion resistance of the magnetic metal powder 22 can be enhanced.

The impurity content is preferably 1.0 at % or less in total of all elements. At this level, the effect of the magnetic metal powder 22 is not impaired even if it contains impurities.

The constituent elements and composition of the magnetic metal powder 22 can be determined by an ICP emission spectrometry method specified in JIS G 1258:2014, a spark emission spectrometry method specified in JIS G 1253:2002, or the like. When the magnetic metal powder 22 is coated with the coating layer 24, the measurement can be performed by the above method after removing the coating layer 24 by a chemical or physical method. When it is difficult to remove the coating layer 24, for example, after cutting the magnetic bead 2, a portion of the magnetic metal powder 22 that is a core can be analyzed using an analyzer such as EPMA (Electron Probe Micro Analyzer) or EDX (Energy Dispersive X-ray spectroscopy).

The Vickers hardness of the magnetic metal powder 22 is preferably 100 or more, more preferably 300 or more, and even more preferably 800 or more. A method for measuring the hardness of the magnetic metal powder 22 is, for example, as follows. After a resin-embedded sample is prepared by taking out a plurality of particles of the magnetic metal powder 22 and embedding them in a resin, a cross section of the magnetic metal powder 22 is made to appear on the surface of the resin-embedded sample by grinding and polishing. An indentation is made on this with a micro Vickers tester or a nanoindenter or the like, and the hardness is determined from the size thereof.

When the Vickers hardness of the magnetic metal powder 22 is less than the above lower limit, the magnetic metal powder 22 may undergo plastic deformation due to an impact when the magnetic bead 2 collides. When plastic deformation occurs, the coating layer 24 may be peeled off or fallen off. The upper limit of the Vickers hardness is not particularly limited, but is preferably 3000 or less from the viewpoint of ease of selection of a material suitable for the balance between performance and cost.

A main metal structure that forms the magnetic metal powder 22 can have various forms such as a crystalline structure, an amorphous structure, and a nanocrystalline structure. The amorphous structure refers to a structure in which no crystals are present, and the nanocrystalline structure refers to a structure mainly containing fine crystals having a crystal grain size of 100 nm or less. In particular, the magnetic metal powder 22 preferably contains an amorphous structure or a nanocrystalline structure. An amorphous structure and a nanocrystalline structure provide a high hardness to the magnetic metal powder 22. Further, by adopting an amorphous structure or a nanocrystalline structure, the coercive force Hc of the magnetic bead 2 becomes a particularly low value, which contributes to the improvement of the redispersibility of the magnetic bead 2. The volume fraction of the amorphous structure or the nanocrystalline structure in the magnetic metal powder 22 is preferably 40% or more, and more preferably 60% or more. The volume fraction is obtained from the result of a crystal structure analysis by X-ray diffraction. Further, the crystalline structure, the amorphous structure, and the nanocrystalline structure may each exist independently, or may form a structure in which two or more of them are mixed.

The metal structure of the magnetic metal powder 22 can be identified by subjecting the magnetic metal powder 22 to a crystal structure analysis by X-ray diffractometry. Furthermore, it can be specified by analyzing a structure observation image or a diffraction pattern of a cut sample with a transmission electron microscope (TEM). More specifically, in the case of an amorphous structure, for example, a diffraction peak derived from a metal crystal such as an $\alpha$-Fe phase is not observed in a peak analysis by X-ray diffractometry. In addition, in the case of an amorphous structure, a so-called halo pattern is formed in an electron beam diffraction pattern by TEM, and formation of a spot due to a crystal is not observed. The nanocrystalline structure is made of a crystalline structure having a grain size of, for example, 100 nm or less, and can be confirmed from a TEM observation image. More precisely, the average grain size can be calculated by image processing or the like from a plurality of TEM structure observation images in which a plurality of crystals are present. The crystal grain size can be estimated by a Sherer method from a diffraction peak of a target crystal phase by X-ray diffractometry. Furthermore, for a crystalline structure with a large grain size, the crystal grain size can be measured by a method of observing a cross section with an optical microscope or a scanning electron microscope (SEM), or the like.

In order to obtain an amorphous structure and a nanocrystalline structure, when the magnetic metal powder 22 is produced, it is effective to increase the cooling rate in cooling after pulverizing a molten raw material. In addition, the ease of formation of an amorphous structure and a nanocrystalline structure also depends on the alloy composition. As a specific alloy composition suitable for forming an amorphous structure and a nanocrystalline structure, a composition in which one or more types selected from the group consisting of Cr, Si, B, C, P, Nb, and Cu is added to Fe is preferred.

1.1.2. Coating Layer

The coating layer 24 coats the particle surface of the magnetic metal powder 22 as shown in FIG. 2. The coating layer 24 may be formed on at least part of the particle surface of the magnetic metal powder 22, but preferably coats the entire particle surface.

The main function of the coating layer 24 is to adsorb a biological material. From this point of view, the coating layer 24 is made of a first oxide material.

Examples of the first oxide material include silicon oxide, aluminum oxide, titanium oxide, vanadium oxide, niobium oxide, chromium oxide, manganese oxide, tin oxide, and zirconium oxide. Among these, one type or a mixture of two or more types is used.

Among these, the first oxide material preferably contains silicon oxide. Silicon oxide is particularly a substance suitable for extraction of a nucleic acid such as DNA or RNA, and its compositional formula is preferably, for example, $SiO_x$ ($0<x\leq 2$), and is specifically preferably $SiO_2$. Such silicon oxide specifically adsorbs a nucleic acid in an aqueous solution in which a chaotropic substance is present, thereby enabling extraction and recovery of the nucleic acid. The "chaotropic substance" is a substance that has an effect of increasing the water solubility of a hydrophobic molecule and contributes to nucleic acid adsorption. Specific examples of the chaotropic substance include guanidine hydrochloride, sodium iodide, and sodium perchlorate.

The first oxide material may contain silicon and an oxide of one type selected from the group consisting of Al, Ti, V, Nb, Cr, Mn, Sn, and Zr, or a composite oxide or a composite of two or more types selected from the group. Al, Ti, V, Nb, Cr, Mn, Sn, and Zr are elements having excellent so-called elution resistance that suppress ion elution from the magnetic metal powder 22 to be coated. Therefore, by using an oxide or a composite oxide or a composite of such an element as the coating layer 24, it is possible to improve the extraction performance of a biological material while ensuring elution resistance. In the coating layer 24, a plurality of layers may be formed from oxides of different elements or the like.

It is desirable that the coating layer 24 does not capture a material that is not an extraction target such as a contaminant. From this point of view, the coating layer 24 preferably contains a substance called a so-called blocking substance together with a preferred substance that the coating layer 24 contains. Examples of the blocking substance include polyethylene glycol, albumin, and dextrin.

The coating layer 24 may contain a substance (impurity) other than the first oxide material as long as the effect thereof is not impaired, for example, in a proportion of 50 mass % or less of the first oxide material. For example, when silicon oxide is used as the first oxide material, examples of the impurity include C, N, and P.

The composition of the first oxide material can be confirmed by, for example, an EDX analysis, Auger electron spectrometry, or the like.

The structure of the coating layer 24 in the depth direction of the magnetic bead 2 may be any structure including a single layer made of a single substance, a single layer made of a plurality of substances, a composite, or a mixture, or a plurality of layers having different compositions. Further, the surface of the coating layer 24 may be formed from either a single substance or a plurality of substances.

The average thickness t2 of the coating layer 24 is preferably 1 nm or more and 200 nm or less, more preferably 2 nm or more and 100 nm or less, and even more preferably 3 nm or more and 50 nm or less. According to this, even if the magnetic beads 2 collide with each other or collide with the inner wall of the container or the like, it is possible to prevent the coating layer 24 from breaking or peeling off. As a result, it is possible to suppress deterioration of the extraction efficiency of the biological material or generation of a contaminant when the biological material is taken out. Further, elution of iron ions or the like due to the exposure of the magnetic metal powder 22 can be suppressed. Moreover, it is possible to suppress a decrease in magnetization per volume of the magnetic bead 2 and suppress a decrease in the moving speed of the magnetic bead 2.

A method for forming such a coating layer 24 will be described in detail later, but examples thereof include a wet forming method such as a sol-gel method and a dry forming method such as a vapor deposition method.

1.2. Oxide Powder

The oxide powder 3 has a particle surface made of a second oxide material and has a function of adsorbing a biological material.

Examples of the second oxide material include silicon oxide, aluminum oxide, titanium oxide, vanadium oxide, niobium oxide, chromium oxide, manganese oxide, tin oxide, and zirconium oxide, and among these, one type or a mixture of two or more types is used.

In this embodiment, the entire particle of the oxide powder 3 is made of the second oxide material. This facilitates the production, quality control, and cost reduction of the oxide powder 3. The second oxide material only needs to form at least the particle surface of the oxide powder 3, and as described later, the inside of the particle of the oxide powder 3 may be made of a material other than the second oxide material.

The second oxide material preferably contains silicon oxide. According to this, the oxide powder 3 becomes a powder particularly suitable for extracting a nucleic acid such as DNA or RNA similarly to the coating layer 24 described above. That is, similarly to the coating layer 24, the oxide powder 3 containing silicon oxide also specifically adsorbs a nucleic acid in an aqueous solution in which a chaotropic substance is present, thereby enabling extraction and recovery of the nucleic acid. Examples of the oxide powder 3 containing silicon oxide include fumed silica and colloidal silica.

In addition, the second oxide material may also contain silicon and an oxide of one type selected from the group consisting of Al, Ti, V, Nb, Cr, Mn, Sn, and Zr, or a composite oxide or a composite of two or more types selected from the group.

It is desirable that also the oxide powder 3 does not capture a material that is not an extraction target such as a contaminant similarly to the coating layer 24. From this point of view, the oxide powder 3 preferably contains a substance called a blocking substance.

The oxide powder 3 may contain an unavoidable impurity as long as the effect thereof is not impaired. For example, when silicon oxide is used as the second oxide material, examples of the unavoidable impurity include C, N, and P.

The composition of the second oxide material can be confirmed by, for example, an EDX analysis, Auger electron spectrometry, or the like.

The average particle diameter d3 of the oxide powder 3 is smaller than the average particle diameter d2 of the magnetic bead 2. According to this, as shown in FIG. 3, when the associated body 4 is formed by associating the magnetic bead 2 with a plurality of particles of the oxide powder 3 through the nucleic acid 9, the specific surface area of the associated body 4 can be increased. As a result, the adsorption amount of the nucleic acid 9 can be increased, and the yield of the nucleic acid 9 can be finally increased.

Specifically, the average particle diameter d3 of the oxide powder 3 is preferably 0.02 μm or more and 0.5 μm or less, and more preferably 0.05 μm or more and 0.3 μm or less. When the average particle diameter d3 of the oxide powder 3 is within the above range, the specific surface area of the oxide powder 3 can be sufficiently increased. According to this, a sufficient amount of the nucleic acid 9 is adsorbed to the oxide powder 3, and the yield of the nucleic acid 9 can be increased. Further, excessive aggregation of the oxide powder 3 can be suppressed so as to facilitate the formation of the associated body 4.

The average particle diameter d3 of the oxide powder 3 can be determined from an integrated distribution curve obtained from a volume-based particle size distribution measured by a laser diffraction/dispersion method. Specifically, the average particle diameter d3 of the oxide powder 3 is a particle diameter D50 (median diameter) at which the cumulative value from the smaller diameter side in the integrated distribution curve is 50%. Examples of an apparatus for measuring the particle size distribution by a laser diffraction/dispersion method include Microtrac MT3000II series manufactured by MicrotracBEL Corp. When the measurement by the laser diffraction/dispersion method is difficult, a technique such as an image analysis may be used.

1.3. Average Particle Diameter of Each of Magnetic Bead and Oxide Powder

In addition, as shown in FIG. 4, there exists a preferred combination between the average particle diameter d3 of the oxide powder 3 and the average particle diameter d2 of the magnetic bead 2.

FIG. 4 is a graph showing a relationship between the average particle diameter d2 of the magnetic bead 2 and the average particle diameter d3 of the oxide powder 3. In FIG. 4, the average particle diameter d2 of the magnetic bead 2 is assigned to the horizontal axis, and the average particle diameter d3 of the oxide powder 3 is assigned to the vertical axis. Further, in FIG. 4, the average particle diameter d2 of the magnetic bead 2 and the average particle diameter d3 of the oxide powder 3 are each divided into a plurality of ranges. A combination of the average particle diameter d2 of the magnetic bead 2 and the average particle diameter d3 of the oxide powder 3 falls within any of the ranges shown in FIG. 4. Hereinafter, effects and problems exhibited by the biological material extraction carrier 1 when this combination falls within each range will be described.

A range A1 shown in FIG. 4 represents a combination example when the average particle diameter d2 of the magnetic bead 2 is set to an arbitrary value and the average particle diameter d3 of the oxide powder 3 is set to less than 0.02 μm.

When each average particle diameter is set to fall within this range A1, the oxide powder 3 is too small. Therefore, the specific surface area of the associated body 4 cannot be sufficiently increased, and the yield of the nucleic acid 9 may not be sufficiently increased.

A range A2 shown in FIG. 4 represents a combination example when the average particle diameter d2 of the magnetic bead 2 is set to less than 0.5 μm and the average particle diameter d3 of the oxide powder 3 is set to 0.02 μm or more. When each average particle diameter is set to fall within this range A2, the magnetic bead 2 is too small. In this case, the saturation magnetization of the magnetic bead 2 decreases, and even if an external magnetic field acts, the magnetic attractive force may not sufficiently increase. Therefore, the time required for magnetic separation may increase.

A range A3 shown in FIG. 4 represents a combination example when the average particle diameter d2 of the magnetic bead 2 is set to 0.5 μm or more and 50 μm or less and the average particle diameter d3 of the oxide powder 3 is set to 0.02 μm or more and 0.5 μm or less. When each average particle diameter is set to fall within this range A3, the average particle diameter d3 of the oxide powder 3 is optimized with respect to the average particle diameter d2 of the magnetic bead 2. According to this, for example, the associated body 4 in which particles of the oxide powder 3 having an appropriate size are associated with one magnetic bead 2 can be formed. As a result, from the viewpoint of the separation speed of the associated body 4 in magnetic separation, the magnetic attractive force generated in the magnetic bead 2 becomes dominant. In addition, from the viewpoint of the specific surface area of the associated body 4, the specific surface area of the oxide powder 3 contributes sufficiently. In that case, the separation speed in magnetic separation can be increased, and the biological material extraction carrier 1 capable of extracting the nucleic acid 9 in high yield can be realized. Further, by optimizing the average particle diameter d2 of the magnetic bead 2 and the average particle diameter d3 of the oxide powder 3, the oxide powder 3 enters a gap between the magnetic beads 2, and therefore, it is possible to prevent a liquid from remaining in the gap. That is, it is possible to reduce the amount of a liquid that adheres to the fixed biological material extraction carrier 1 and remains without being discharged (residual liquid amount). This can suppress deterioration of the separability of the solid phase and the liquid phase in magnetic separation.

A range A4 shown in FIG. 4 represents a combination example when the average particle diameter d2 of the magnetic bead 2 is set to more than 50 μm and the average particle diameter d3 of the oxide powder 3 is set to 0.02 μm or more and 0.5 μm or less. When each average particle diameter is set to fall within this range A4, the magnetic bead 2 is too large. Therefore, the specific surface area of the magnetic bead 2 decreases, and along with this, the specific surface area of the associated body 4 cannot be sufficiently increased, and the yield of the nucleic acid 9 may not be sufficiently increased. In addition, a gap between the magnetic beads 2 becomes large, and therefore, a liquid tends to remain in the gap, and the separability of the solid phase and the liquid phase in magnetic separation may deteriorate.

A range A5 shown in FIG. 4 represents a combination example when the average particle diameter d2 of the magnetic bead 2 is set to 0.5 μm or more and the average particle diameter d3 of the oxide powder 3 is set to more than 0.5 μm.

When each average particle diameter is set to fall within this range A5, the oxide powder 3 is too large. Therefore, it tends to become difficult to form the associated body 4 of the magnetic bead 2 and the oxide powder 3. On the other hand, the particles of the oxide powder 3 may form an associated body with each other through the nucleic acid 9. Such an associated body does not contain the magnetic bead 2, and therefore is not captured by an external magnetic field. Therefore, when each average particle diameter is set to fall within this range A5, the yield of the nucleic acid 9 may decrease.

1.4. Particle Diameter Ratio and Volume Ratio

Further, even in the range A3 shown in FIG. 4, there exists a preferred range for the ratio of the average particle diameter d3 of the oxide powder 3 to the average particle diameter d2 of the magnetic bead 2 (d3/d2).

The ratio of the average particle diameter d3 to the average particle diameter d2 (particle diameter ratio) is preferably 0.1% or more and 40.0% or less, more preferably 0.5% or more and 20.0% or less, and even more preferably 1.0% or more and 10.0% or less. By setting the particle diameter ratio within the above range, the effect when setting each average particle diameter to fall within the range A3 becomes more pronounced. That is, the separation speed in magnetic separation can be particularly increased, and the biological material extraction carrier 1 capable of extracting the nucleic acid 9 in particularly high yield can be realized. Further, it is possible to prevent a liquid from remaining in the gap between the magnetic beads 2, thereby reducing the residual liquid amount.

Further, in the biological material extraction carrier 1, when the volume of the magnetic bead 2 is represented by v2 and the volume of the oxide powder 3 is represented by v3, the volume ratio defined by v3/v2 is preferably 0.1% or more and 40.0% or less, more preferably 1.0% or more and 35.0% or less, and even more preferably 10.0% or more and 25.0% or less. By setting the volume ratio within the above range, the quantitative balance between the magnetic bead 2 and the oxide powder 3 is optimized. This facilitates, for example, the formation of the associated body 4 in which an appropriate number of particles of the oxide powder 3 are associated with one magnetic bead 2. As a result, both the separation speed of the associated body 4 in magnetic separation and the specific surface area of the associated body 4 can be achieved. In that case, when the biological material extraction carrier 1 is used for the extraction of a biological material using magnetic separation, the time required for magnetic separation can be shortened and the yield of the biological material can be increased.

Figure 5:
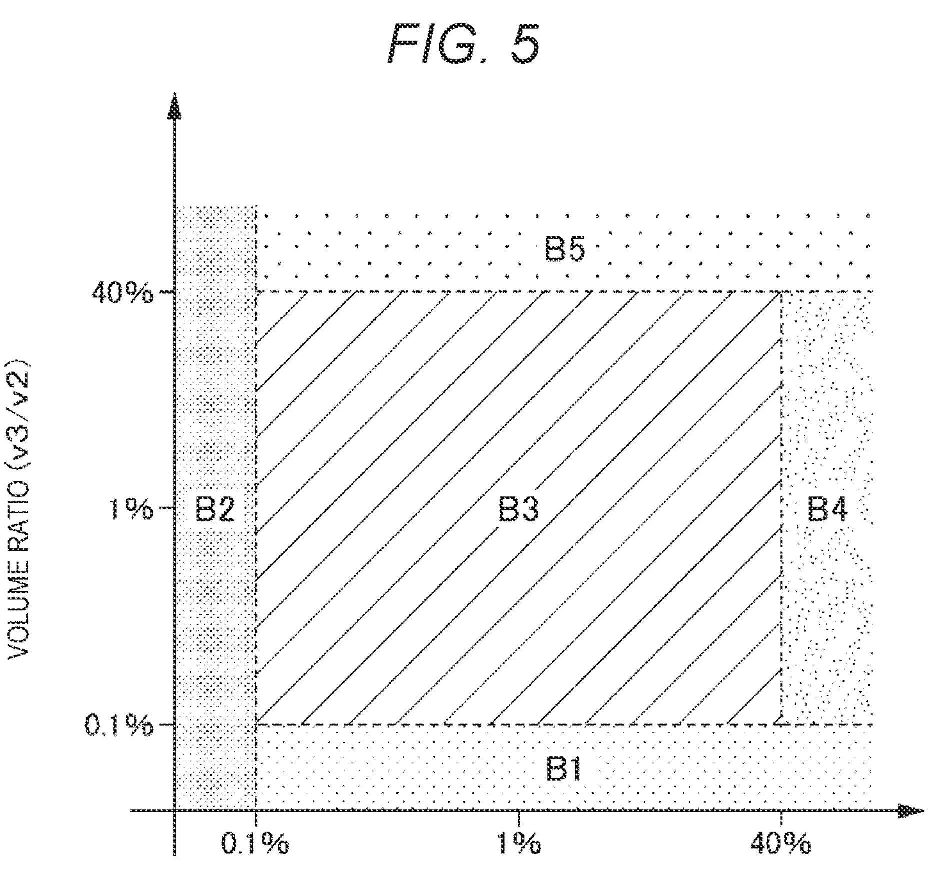
FIG. 5 is a graph showing a relationship between a particle diameter ratio (ratio of d3/d2) and a volume ratio (ratio of v3/v2).

FIG. 5 is a graph showing a relationship between the particle diameter ratio (ratio of d3/d2) and the volume ratio (ratio of v3/v2). In FIG. 5, the particle diameter ratio is assigned to the horizontal axis, and the volume ratio is assigned to the vertical axis. Further, in FIG. 5, the particle diameter ratio and the volume ratio are each divided into a plurality of ranges. A combination of the particle diameter ratio and the volume ratio falls within any of the ranges shown in FIG. 5. Hereinafter, effects and problems exhibited by the biological material extraction carrier 1 when this combination falls within each range will be described.

A range B1 shown in FIG. 5 represents a combination example when the particle diameter ratio is set to 0.1% or more and the volume ratio is set to less than 0.1%. When the particle diameter ratio and the volume ratio are set to fall within this range B1, the amount of the oxide powder 3 is relatively too small even if the particle diameter ratio is appropriate. Due to this, the specific surface area of the associated body 4 cannot be sufficiently increased, and the yield of the nucleic acid 9 may not be sufficiently increased.

A range B2 shown in FIG. 5 represents a combination example when the particle diameter ratio is set to less than 0.1% and the volume ratio is set to an arbitrary value. When the particle diameter ratio and the volume ratio are set to fall within this range B2, the oxide powder 3 is too small regardless of the volume ratio. Therefore, the specific surface area of the associated body 4 cannot be sufficiently increased, and the yield of the nucleic acid 9 may not be sufficiently increased.

A range B3 shown in FIG. 5 represents a combination example when the particle diameter ratio is set to 0.1% or more and 40.0% or less and the volume ratio is set to 0.1% or more and 40.0% or less. When the particle diameter ratio and the volume ratio are set to fall within this range B3, both are optimized. Among them, by optimizing the particle diameter ratio, for example, it is possible to form the associated body 4 in which particles of the oxide powder 3 having an appropriate size are associated with one magnetic bead 2. In addition, by optimizing the volume ratio, for example, it becomes easy to form the associated body 4 in which an appropriate number of particles of the oxide powder 3 are associated with one magnetic bead 2. As a result, both the separation speed of the associated body 4 in magnetic separation and the specific surface area of the associated body 4 can be achieved.

A range B4 shown in FIG. 5 represents a combination example when the particle diameter ratio is set to more than 40.0% and the volume ratio is set to 0.1% or more and 40.0% or less. When the particle diameter ratio and the volume ratio are set to fall within this range B4, the oxide powder 3 is too large even if the volume ratio is appropriate. Therefore, it tends to become difficult to form the associated body 4 of the magnetic bead 2 and the oxide powder 3. On the other hand, the particles of the oxide powder 3 may form an associated body with each other through the nucleic acid 9. Such an associated body does not contain the magnetic bead 2, and therefore is not captured by an external magnetic field. Therefore, when each average particle diameter is set to fall within this range B4, the yield of the nucleic acid 9 may decrease.

A range B5 shown in FIG. 5 represents a combination example when the particle diameter ratio is set to 0.1% or more and the volume ratio is set to more than 40.0%. When the particle diameter ratio and the volume ratio are set to fall within this range B5, the amount of the oxide powder 3 is relatively too large even if the particle diameter ratio is appropriate. Therefore, the oxide powder 3 which becomes surplus is generated, and the particles of the oxide powder 3 may form an associated body with each other. Such an associated body does not contain the magnetic bead 2, and therefore is not captured by an external magnetic field. In that case, the nucleic acid 9 adsorbed to such an associated body cannot be extracted, and the yield of the nucleic acid 9 may decrease.

1.5. Modification of Oxide Powder

Next, a modification of the oxide powder 3 will be described.

Figure 6:
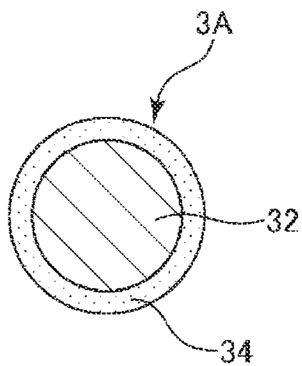
FIG. 6 is a cross-sectional view showing a modification of an oxide powder in FIG. 1.

FIG. 6 is a cross-sectional view showing a modification of the oxide powder 3 in FIG. 1.

As shown in FIG. 6, a particle of an oxide powder 3A according to the modification is a particle having a core portion 32 and a coating layer 34 (second coating layer) that coats the surface thereof. That is, the particle of the oxide powder 3 shown in FIG. 1 has a uniform structure as a whole, whereas the particle of the oxide powder 3A according to this modification has a so-called core-shell structure. Hereinafter, with respect to the oxide powder 3A according to the modification, different points from the oxide powder 3 will be mainly described, and the description of the same matters as those of the oxide powder 3 will be omitted.

The particle shape and particle size distribution of the oxide powder 3A having a core-shell structure depend on the core portion 32, while the adsorbability of a biological material to the surface depends on the coating layer 34. Therefore, if the coating layer 34 can be formed from the above-mentioned second oxide material, the oxide powder 3A can be realized, and the ease of production of the oxide powder 3A can be enhanced. That is, various existing deposition methods can be adopted for forming the coating layer 34, and the core portion 32 having an excellent particle shape and particle size distribution is easily obtained, and therefore, the oxide powder 3A having excellent properties can be realized at low cost.

The constituent material of the core portion 32 is not particularly limited, but may be any material different from the constituent material of the coating layer 34, and examples thereof include organic materials such as a resin material and inorganic materials such as a carbon material, a silicon material, and a glass material.

The constituent material of the coating layer 34 is the second oxide material described above. In addition, examples of a method for forming the coating layer 34 include the same method as the method for forming the coating layer 24 described above.

The average particle diameter of the oxide powder 3A is the same as the average particle diameter d3 of the oxide powder 3 described above.

Further, when the average thickness of the coating layer 34 is represented by t3 and the average particle diameter of the oxide powder 3A is represented by d3, the ratio of t3 to d3: t3/d3 is preferably 0.0001 or more, and more preferably 0.001 or more and 0.1 or less. When t3/d3 is less than the above lower limit, the ratio of the thickness of the coating layer 34 to the size of the core portion 32 becomes too small, and therefore, when an impact or the like is applied to the particles of the oxide powder 3A, the coating layer 34 may be broken or peeled off, resulting in contaminants (contamination) when the biological material is taken out. On the other hand, t3/d3 may exceed the above upper limit, but in that case, it takes time to form the coating layer 34, and therefore, the advantage of the oxide powder 3A may not be fully enjoyed.

The average thickness t3 of the coating layer 34 is not limited to the above description, and is preferably 1 nm or more and 200 nm or less, more preferably 2 nm or more and 100 nm or less, and even more preferably 3 nm or more and 50 nm or less.

The thickness of the coating layer 34 can be measured, for example, from a cross-sectional observation image of the particle of the oxide powder 3A by a transmission electron microscope, a scanning electron microscope, or the like. Also, the average thickness t3 of the coating layer 34 can be calculated by obtaining a plurality of observation images and averaging the measured values from image processing or the like. For example, the average thickness t3 is a value obtained by measuring the thickness of the coating layer 34 at 5 or more locations for one particle, calculating the average value, and then averaging the average values for 10 or more particles.

2. Method for Producing Biological Material Extraction Carrier

Next, an example of a method for producing the biological material extraction carrier 1 will be described.

The biological material extraction carrier 1 includes the magnetic bead 2 and the oxide powder 3 or the oxide powder 3A as described above.

Here, an example of a method for producing the magnetic bead 2 will be described.

The method for producing the magnetic bead 2 includes a magnetic metal powder production step of producing the magnetic metal powder 22, a classification step of classifying the magnetic metal powder 22 so as to have a predetermined particle diameter and particle size distribution, and a coating layer forming step of forming the coating layer 24 on the magnetic metal powder 22 that has undergone the classification step. Hereinafter, the respective steps will be described.

2.1. Magnetic Metal Powder Production Step

The magnetic metal powder 22 is produced by a method according to a general method for producing a metal powder. Examples of the production method include a melting process in which a metal is melted and solidified into a powder, a chemical process in which a powder is produced by a reduction method or a carbonyl method, and a mechanical process in which a powder is obtained by mechanically pulverizing a material with a larger shape such as an ingot. Among these, the melting process is suitable for producing the magnetic metal powder 22.

An atomization method is a representative production method among the production methods using a melting process. This involves spraying a molten metal having a desired composition formed by melting into a powder.

The atomization method is a method in which a molten metal is allowed to collide with a fluid (a liquid or a gas) jetted at a high speed to rapidly solidify into a powder, and is divided into a water atomization method, a high-pressure water atomization method, a spinning water atomization method, a gas atomization method, and the like according to the type of cooling medium and the apparatus configuration. The magnetic metal powder 22 can be efficiently produced by producing the metal powder with such an atomizing method. Further, in a high-pressure water atomization method, a spinning water atomization method, or a gas atomization method, the particle shape of the metal powder becomes nearly spherical due to the action of surface tension. Among these, in a high-pressure water atomization method or a high-speed spinning water atomization method, fine droplets of molten metal are formed, which are then rapidly solidified by a high-speed water flow, whereby a quenched powder with a nearly spherical shape and a fine particle diameter can be obtained. In these production methods, the molten metal can be cooled at an extremely high cooling rate of about $10^3$ to $10^7$° C./sec, and therefore, solidification can be achieved in a state where the disordered atomic arrangement in the molten metal is highly maintained. Therefore, a powder containing an amorphous structure can be efficiently produced. In addition, by appropriately performing a heat treatment for the thus obtained amorphous powder, a powder containing a nanocrystalline structure can be obtained.

As the production method using a chemical process, a carbonyl method is a representative example and is particularly known as a production method for obtaining a spherical powder of pure Fe or pure Ni. In particular, a pure Fe powder obtained by a carbonyl method has a high saturation magnetization. On the other hand, particles produced by a carbonyl method may not have a sufficient Vickers hardness.

After the magnetic metal powder 22 is produced as described above, a classification step is performed as needed, and then, a coating layer forming step is performed. The order of the classification step and the coating layer forming step may be reversed.

2.2. Classification Step

In the classification step, the magnetic metal powder 22 obtained in the magnetic metal powder production step is classified to adjust the particle diameter and the particle size distribution.

Examples of a classification method include a method using a sieve, a method using a difference in moving distance due to a centrifugal force in a fluid such as air or water, and a method using a difference in precipitation speed due to gravity in a fluid (gravity classification). In the classification in a fluid, classification performed in a gas such as air is generally referred to as dry classification (pneumatic classification), and classification performed in a liquid such as water is generally referred to as wet classification. Classification by a so-called cyclone method or rotor method, or the like using a difference in moving distance due to a centrifugal force is used in both dry classification and wet classification, but classification in a liquid is more preferred from the viewpoint of improving dispersibility in a fluid and suppressing aggregation of particles.

2.3. Coating Layer Forming Step

In the coating layer forming step, the coating layer 24 is formed on the particle surface of the magnetic metal powder 22.

A method for forming the coating layer 24 is not particularly limited, but examples thereof include wet forming methods such as a sol-gel method and a coupling agent treatment, and dry forming methods such as an ALD (Atomic Layer Deposition) method, a CVD (Chemical Vapor Deposition) method, and ion plating. Among these, in the formation of the coating layer 24 made of an oxide material, a Stober method, which is a kind of sol-gel method or the above-mentioned ALD method can be mainly used.

The Stober method is a method for forming monodispersed particles by hydrolysis of a metal alkoxide. When the coating layer 24 is formed from silicon oxide, the coating layer 24 can be formed by a hydrolysis reaction of a silicon alkoxide.

Specifically, first, the magnetic metal powder 22 is dispersed in an alcohol solution containing a silicon alkoxide. Examples of the alcohol solution include lower alcohols such as ethanol and methanol. The addition ratio of the alcohol to the silicon alkoxide may be set to, for example, 10 parts by weight or more and 50 parts by weight or less with respect to 1 part by weight of tetraethoxysilane. Further, the addition ratio of the silicon alkoxide to the magnetic metal powder 22 may be set to 0.01 parts by weight or more and 0.1 parts by weight or less when the amount of the magnetic metal powder 22 is set to 1 part by weight.

Examples of the silicon alkoxide include TMOS (tetramethoxysilane), TEOS (tetraethoxysilane), tetraisopropoxysilane, tetrapropoxysilane, tetrakis(trimethylsilyloxy)silane, tetrabutoxysilane, tetraphenoxysilane, and tetrakis(2-ethylhexyloxy)silane. As the silicon alkoxide, particularly, TEOS is preferably used.

Subsequently, as a catalyst for promoting the reaction, aqueous ammonia is supplied to cause hydrolysis. As a result, a dehydration-condensation reaction occurs between the hydrolysates or between the hydrolysate and the silicon alkoxide, and a —Si—O—Si— bond is formed on the particle surface, thereby forming a silicon oxide film.

Before and after supplying the aqueous ammonia, it is preferred to stir the magnetic metal powder 22 and the alcohol solution using an ultrasonic wave applicator or the like. By stirring in each step in this manner, uniform dispersion of the particles is promoted, and also a silicon oxide film can be uniformly formed on the particle surface. Stirring is preferably performed for a time equal to or longer than the time required for the hydrolysis reaction of the silicon alkoxide to proceed sufficiently.

In the above description, the magnetic metal powder 22 is dispersed in the alcohol solution containing the silicon alkoxide, and then, the aqueous ammonia is supplied. However, the order is not limited thereto. For example, the order may be such that the aqueous ammonia is mixed with the alcohol solution in which the magnetic metal powder 22 is dispersed, and then, the alcohol solution containing the silicon alkoxide is mixed therewith. In such a case, the alcohol solution containing the silicon alkoxide may be added in several portions. When adding the solution in several portions, the above-mentioned stirring may be performed each time the addition is made, or the addition is made to the solution under stirring.

In addition, triethylamine, triethanolamine, or the like may be used as a material having the same effect as the aqueous ammonia.

When the thickness of the coating layer 24 is adjusted, the proportion of the silicon alkoxide in the solution may be appropriately changed. For example, by increasing the proportion of the silicon alkoxide in the solution, the thickness of the coating layer 24 is increased.

The magnetic bead 2 is obtained through the above steps, but the obtained magnetic bead 2 may be subjected to a heat treatment for further improving the performance. For example, by heating at a temperature of 60° C. or higher and 300° C. or lower for 10 minutes or more and 300 minutes or less, the hydrate remaining in the magnetic bead 2 can be removed and the strength of the magnetic bead 2 can be improved.

On the other hand, the ALD method is also a suitable method for forming a silicon oxide coating film. As a specific method for forming a silicon oxide coating film by the ALD method, a method in which the magnetic metal powder 22 is put into a chamber that can be evacuated and can control the atmosphere, and also a substance called a precursor for forming a silicon oxide film, specifically dimethylamine, methylethylamine, diethylamine, tris(dimethylamino)silane, bis(diethylamino)silane, bis(tertiarybutylamino)silane, or the like, is put into the chamber, followed by thermal decomposition, thereby forming silicon oxide on the particle surface of the magnetic metal powder 22 is exemplified. According to the ALD method, it is possible to form the coating layer 24 which is dense and thin by depositing the raw material at the atomic layer level.

Further, by selecting the precursor, it is also possible to form an oxide layer other than silicon oxide, or a coating layer made of a composite oxide.

3. Effect of the Biological Material Extraction Carrier According to Embodiment As described above, the biological material extraction carrier 1 according to the embodiment includes the magnetic bead 2 and the oxide powder 3. The magnetic bead 2 includes the magnetic metal powder 22 and the coating layer 24 (first coating layer) that coats the particle surface thereof. The coating layer 24 is made of the first oxide material. Further, the oxide powder 3 is a powder in which the particle surface is made of the second oxide material and the average particle diameter is smaller than that of the magnetic bead 2.

When a biological material is extracted using such a biological material extraction carrier 1, for example, as shown in FIG. 3, it is possible to form the associated body 4 in which the magnetic bead 2 and a plurality of particles of the oxide powder 3 are associated through the nucleic acid 9 (biological material) in a liquid containing the nucleic acid 9. Such an associated body 4 contains a plurality of particles of the oxide powder 3, and therefore has a large specific surface area and adsorbs a large amount of the nucleic acid 9. On the other hand, since the associated body 4 contains the magnetic bead 2, even if it contains the oxide powder 3 having no magnetism, it can be captured by an external magnetic field. Then, in the associated body 4, a plurality of particles of the oxide powder 3 smaller than the magnetic bead 2 are contained, and therefore, even if the size of the magnetic bead 2 is increased, a decrease in the specific surface area can be suppressed. Therefore, the magnetic bead 2 having a large particle diameter and a high saturation magnetization can be used, and the magnetic attractive force of the associated body 4 can be increased. As a result, according to the biological material extraction carrier 1, the nucleic acid 9 can be extracted and recovered in high yield while increasing the separation speed in magnetic separation. Further, according to the biological material extraction carrier 1, in particular, even when the nucleic acid 9 has a small molecular weight, a high yield can be ensured.

In addition, the oxide powder 3 enters a gap between the magnetic beads 2 so as to reduce the gap, and therefore, the amount of a liquid remaining in the gap (residual liquid amount) after magnetic separation can be reduced.

The average particle diameter d2 of the magnetic bead 2 is preferably 0.5 μm or more and 50 μm or less. According to this, the specific surface area of the magnetic bead 2 can be sufficiently increased, and the mass and saturation magnetization of the magnetic bead 2 are suitable for magnetic separation. Further, aggregation of the magnetic beads 2 can be suppressed, and redispersibility can be enhanced.

The average particle diameter d3 of the oxide powder 3 is preferably 0.1% or more and 40.0% or less of the average particle diameter d2 of the magnetic bead 2. According to this, the average particle diameter d3 of the oxide powder 3 is optimized with respect to the average particle diameter d2 of the magnetic bead 2, and for example, the associated body 4 in which particles of the oxide powder 3 having an appropriate size are associated with one magnetic bead 2 can be formed. As a result, from the viewpoint of the separation speed of the associated body 4 in magnetic separation, the magnetic attractive force generated in the magnetic bead 2 becomes dominant, and from the viewpoint of the specific surface area of the associated body 4, the specific surface area of the oxide powder 3 contributes sufficiently. In that case, the separation speed in magnetic separation can be increased, and the biological material extraction carrier 1 capable of extracting the nucleic acid 9 in high yield can be realized.

The volume v3 of the oxide powder 3 is preferably 0.1% or more and 40.0% or less of the volume v2 of the magnetic bead 2. According to this, the quantitative balance between the magnetic bead 2 and the oxide powder 3 is optimized. For example, it becomes easy to form the associated body 4 in which an appropriate number of particles of the oxide powder 3 are associated with one magnetic bead 2. As a result, both the separation speed of the associated body 4 in magnetic separation and the specific surface area of the associated body 4 can be achieved.

The first oxide material preferably contains silicon oxide. Silicon oxide is particularly a substance suitable for the extraction of a nucleic acid such as DNA or RNA, and enables efficient extraction and recovery of a nucleic acid by specifically adsorbing the nucleic acid in an aqueous solution in which a chaotropic substance is present.

The second oxide material preferably contains silicon oxide. Silicon oxide is particularly a substance suitable for the extraction of a nucleic acid such as DNA or RNA, and enables efficient extraction and recovery of a nucleic acid by specifically adsorbing the nucleic acid in an aqueous solution in which a chaotropic substance is present.

A particle of the oxide powder 3A according to the modification includes the core portion 32 and the coating layer 34 (second coating layer) that coats the surface of the core portion 32 and is made of the second oxide material. According to such an oxide powder 3A, various existing deposition methods can be adopted for forming the coating layer 34, and therefore, the ease of production of the oxide powder 3A can be enhanced. In addition, the core portion 32 having an excellent particle shape and particle size distribution is easily obtained, and therefore, the oxide powder 3A having excellent properties can be realized at low cost.

4. Biological Material Extraction Method

Next, a biological material extraction method according to an embodiment will be described.

Figure 7:
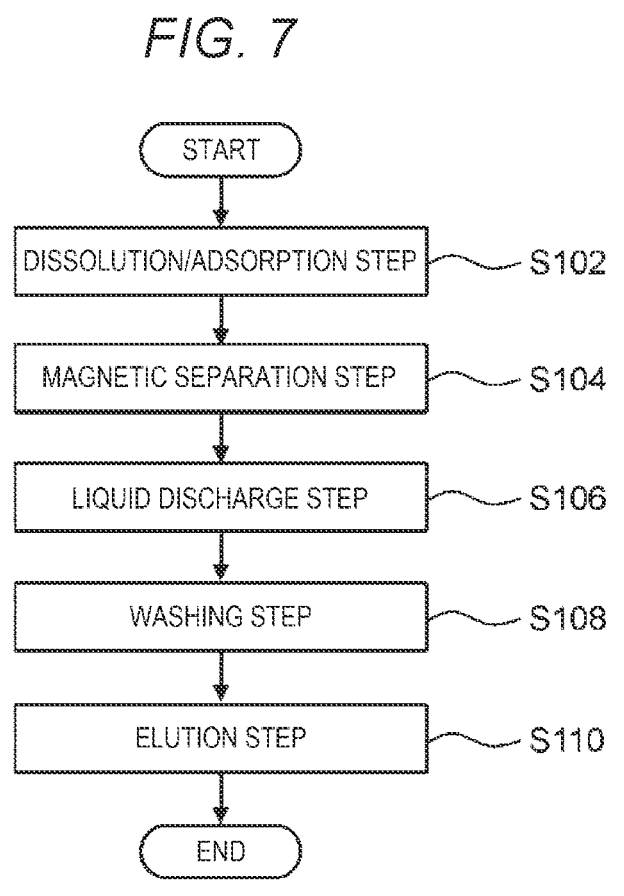

FIG. 7 is a process chart for illustrating the biological material extraction method according to the embodiment.

The biological material extraction method shown in FIG. 7 includes a dissolution/adsorption step S102, a magnetic separation step S104, a liquid discharge step S106, a washing step S108, and an elution step S110. Hereinafter, the respective steps will be sequentially described. In the following description, a case where a nucleic acid is used as a biological material, and the biological material extraction carrier 1 shown in FIG. 1 is used will be described as an example.

4.1. Dissolution/Adsorption Step

In the dissolution/adsorption step S102, first, an analyte sample containing a nucleic acid is placed in a container. In this container, the biological material extraction carrier 1 and a dissolution/adsorption liquid are further placed. Then, the contents of the container are mixed. Thereby, the biological material extraction carrier 1 shown in FIG. 1 is dispersed in the liquid. A nucleic acid is usually enclosed in a cell membrane or a nucleus, and therefore, first, the cell membrane or a so-called outer shell of the nucleus is dissolved and removed by the dissolution action of the dissolution/adsorption liquid to take out the nucleic acid. Thereafter, by the adsorption action of the dissolution/adsorption liquid, the nucleic acid is adsorbed to the surface of the biological material extraction carrier 1, specifically the surface of the magnetic bead 2 or the oxide powder 3. Thus, as shown in FIG. 3, the magnetic bead 2 and the oxide powder 3 are associated through the nucleic acid 9 and the associated body 4 is formed. In this step, dissolution and removal of the outer shell may be omitted. In that case, an adsorption liquid may be used in place of the dissolution/adsorption liquid, and this step may also be an adsorption step.

As the dissolution/adsorption liquid, for example, a liquid containing a chaotropic substance is used. The chaotropic substance produces chaotropic ions in an aqueous solution, and reduces the interaction of water molecules, thereby has an effect of destabilizing the structure, and contributes to the adsorption of a nucleic acid to the magnetic bead 2 or the oxide powder 3. Examples of the chaotropic substance that exists as chaotropic ions in an aqueous solution include guanidine thiocyanate, guanidine hydrochloride, sodium iodide, potassium iodide, and sodium perchlorate. Among these, guanidine thiocyanate or guanidine hydrochloride, which has a strong protein denaturing action, is preferably used.

The concentration of the chaotropic substance in the dissolution/adsorption liquid varies depending on the chaotropic substance, but is preferably, for example, 1.0 M or more and 9.0 M or less. In particular, when using guanidine thiocyanate, it is preferably 5.0 M or more and 7.0 M or less. Further, in particular, when using guanidine hydrochloride, it is preferably 4.0 M or more and 8.0 M or less.

The dissolution/adsorption liquid may contain a surfactant. The surfactant is used for the purpose of disrupting a cell membrane or denaturing a protein contained in a cell. The surfactant is not particularly limited, but examples thereof include nonionic surfactants such as polyoxyethylene sorbitan monolaurate, Triton-series surfactants, and Tween-series surfactants, and anionic surfactants such as sodium N-lauroyl sarcosinate. Among these, a nonionic surfactant is preferably used. A nonionic surfactant reduces the effect of an ionic surfactant when analyzing a nucleic acid after extraction. As a result, an analysis by electrophoresis becomes possible, and the choices of analytical methods can be expanded.

The concentration of the surfactant in the dissolution/adsorption liquid is not particularly limited, but is preferably 0.1 mass % or more and 15.0 mass % or less.

The dissolution/adsorption liquid may contain at least one of a reducing agent and a chelating agent. Examples of the reducing agent include 2-mercaptoethanol and dithiothreitol. Examples of the chelating agent include disodium dihydrogen ethylenediamine tetraacetic acid dihydrate (EDTA).

The concentration of the reducing agent in the dissolution/adsorption liquid is not particularly limited, but is preferably 0.2 M or less. The concentration of the chelating agent in the dissolution/adsorption liquid is not particularly limited, but is preferably 50 mM or less.

The pH of the dissolution/adsorption liquid is not particularly limited, but is preferably a neutral pH of 6 or more and 8 or less. In addition, in order to adjust the pH, tris(hydroxy)aminomethane, HCl, or the like may be added as a buffer solution.

In the dissolution/adsorption step S102, if necessary, the contents of the container are stirred by a vortex mixer, hand shaking, or the like. The stirring time is not particularly limited, but is preferably 5 seconds or more and 40 minutes or less.

4.2. Magnetic Separation Step

In the magnetic separation step S104, the biological material extraction carrier 1 with the nucleic acid 9 adsorbed thereto is subjected to an external magnetic field and magnetically attracted. Thereby, the biological material extraction carrier 1 that forms the associated body 4 described above is moved to the inner wall of the container and fixed thereto. As a result, the biological material extraction carrier 1, which is a solid phase, and the liquid, which is a liquid phase, can be separated.

The magnetic separation step S104 and the below-mentioned liquid discharge step S106 are performed not only after the dissolution/adsorption step S102, but also in the below-mentioned washing step S108 and elution step S110.

Prior to magnetic attraction, the contents of the container are stirred as needed. Thereby, the probability that the nucleic acid is adsorbed to the biological material extraction carrier 1 is increased. In the stirring, for example, a vortex mixer, hand shaking, or the like is used.

In the application of the external magnetic field, for example, a magnet arranged on the side of the container is used. The magnet may be an electromagnet or a permanent magnet. When the external magnetic field acts on the associated body 4, the associated body 4 moves toward the magnet. The moving speed at this time, that is, the separation speed in magnetic separation mainly depends on the saturation magnetization of the magnetic bead 2 included in the associated body 4. On the other hand, the adsorption amount of the nucleic acid mainly depends on the specific surface area of the associated body 4. Therefore, by forming the associated body 4, the separation speed can be increased by increasing the saturation magnetization of the magnetic bead 2 without impairing the adsorption amount of the nucleic acid 9. In addition, the adsorption amount of the nucleic acid 9 can be increased by increasing the specific surface area of the associated body 4 without impairing the separation speed. As a result, the nucleic acid 9 can be extracted and recovered in high yield while increasing the separation speed in magnetic separation.

After performing magnetic separation, an acceleration may be applied to the container as needed. Thereby, the liquid adhering to the biological material extraction carrier 1 can be shaken off, so that the liquid that could not be separated can be reduced. The acceleration may be a centrifugal acceleration. In the application of the centrifugal acceleration, a centrifuge may be used.

4.3. Liquid Discharge Step

In the liquid discharge step S106, the liquid separated from the biological material extraction carrier 1 in the container is discharged with a pipette or the like. Further, if necessary, the liquid adhering to the biological material extraction carrier 1 may be sucked and discharged. After discharging the liquid, the application of the external magnetic field is stopped. Thereby, the fixation of the biological material extraction carrier 1 is released.

4.4. Washing Step

In the washing step S108, the biological material extraction carrier 1 with the nucleic acid 9 adsorbed thereto is washed. The washing refers to an operation in which in order to remove contaminants adsorbed to the biological material extraction carrier 1 that forms the associated body 4 described above, the biological material extraction carrier 1 with the nucleic acid 9 adsorbed thereto is brought into contact with a washing liquid, and then separating it again, thereby removing the contaminants.

Specifically, the washing liquid is supplied into the container using a pipette or the like. Then, the biological material extraction carrier 1 and the washing liquid are stirred. Thereby, the washing liquid comes into contact with the biological material extraction carrier 1 to carry out washing. In the stirring, for example, a vortex mixer, hand shaking, or the like is used. At this time, the external magnetic field may be temporarily removed. Thereby, the biological material extraction carrier 1 is dispersed in the washing liquid, so that the washing efficiency can be further enhanced.

Subsequently, the biological material extraction carrier 1 is subjected to an external magnetic field again and fixed to the inner wall of the container, and then, the washing liquid is discharged. By repeating the supply and discharge of the washing liquid as described above one or more times, contaminants can be accurately removed.

The washing liquid is not particularly limited as long as it is a liquid that does not promote the elution of the nucleic acid 9 nor promote the binding of contaminants to the biological material extraction carrier 1, and examples thereof include organic solvents such as ethanol, isopropyl alcohol, and acetone, an aqueous solution thereof, and a low-salt concentration aqueous solution. Examples of the low-salt concentration aqueous solution include a buffer. The salt concentration of the low-salt concentration aqueous solution is preferably 0.1 mM or more and 100 mM or less, and more preferably 1 mM or more and 50 mM or less. The salt for forming the buffer is not particularly limited, but TRIS, HEPES, PIPES, or a salt of phosphoric acid or the like is preferably used.

The washing liquid may contain a surfactant such as Triton (registered trademark), Tween (registered trademark), or SDS. Further, the washing liquid may contain a chaotropic substance such as guanidine hydrochloride. The pH of the washing liquid is not particularly limited.

The washing step S108 may be performed as needed, and may be omitted when washing is not required.

Also in the washing step S108, the same operations as those in the magnetic separation step S104 and the liquid discharge step S106 described above can be performed.

4.5. Elution Step

In the elution step S110, the nucleic acid 9 adsorbed to the biological material extraction carrier 1 that forms the associated body 4 described above is eluted in an elution liquid. The elution is an operation in which the biological material extraction carrier 1 with the nucleic acid 9 adsorbed thereto is brought into contact with an elution liquid, and then separating it again, thereby transferring the nucleic acid 9 to the elution liquid.

Specifically, first, the elution liquid is supplied into the container using a pipette or the like. Then, the biological material extraction carrier 1 that forms the associated body 4 and the elution liquid are stirred. Thereby, the elution liquid comes into contact with the biological material extraction carrier 1, and the nucleic acid 9 can be eluted in the elution liquid. In the stirring, for example, a vortex mixer, hand shaking, or the like is used. At this time, the external magnetic field may be temporarily removed. Thereby, the biological material extraction carrier 1 is dispersed in the elution liquid, so that the elution efficiency can be further enhanced.

Subsequently, the biological material extraction carrier 1 is subjected to an external magnetic field again and fixed to the inner wall of the container, and then, the elution liquid in which the nucleic acid 9 is eluted is discharged. Thereby, the nucleic acid 9 can be recovered. When the nucleic acid 9 is eluted, the associated body 4 is dissociated, and therefore, the oxide powder 3 is also transferred to the elution liquid along with this. This oxide powder 3 is removed in a step described later.

The elution liquid is not particularly limited as long as it is a liquid that promotes the elution of the nucleic acid 9 from the biological material extraction carrier 1 with the nucleic acid 9 adsorbed thereto, but for example, in addition to water such as sterile water or pure water, TE buffer, that is, an aqueous solution containing 10 mM Tris-HCl buffer and 1 mM EDTA and having a pH of about 8 is preferably used.

The elution liquid may contain a surfactant such as Triton (registered trademark), Tween (registered trademark), or SDS. In addition, the elution liquid may contain sodium azide as a preservative.

Further, in the elution step S110, the elution liquid may be heated. Thereby, the elution of the nucleic acid 9 can be promoted. The heating temperature of the elution liquid is not particularly limited, but is preferably 70° C. or higher and 200° C. or lower, more preferably 80° C. or higher and 150° C. or lower, and even more preferably 95° C. or higher and 125° C. or lower.

Examples of a heating method include a method of supplying a preheated elution liquid, and a method of heating after supplying an unheated elution liquid to a container. The heating time is not particularly limited, but is preferably 30 seconds or more and 10 minutes or less.

Also in the elution step S110, the same operations as those in the magnetic separation step S104 and the liquid discharge step S106 described above can be performed.

Further, an operation of separating the oxide powder 3 from the recovered elution liquid may be performed as needed. In this separation, for example, a centrifugation treatment is used. Thereafter, the separated liquid is recovered. Thereby, the nucleic acid 9 contained in the liquid can be purified. The nucleic acid 9 recovered in this manner is, for example, subjected to a test by a biological material testing method such as a PCR method. This can prevent the oxide powder 3 from being subjected to a test together with the nucleic acid 9.

4.7. Effect of Biological Material Extraction Method According to Embodiment As described above, the biological material extraction method according to the embodiment includes the dissolution/adsorption step S102 (adsorption step) and the elution step S110. In the dissolution/adsorption step S102, the nucleic acid 9 (biological material), the dissolution/adsorption liquid (adsorption liquid), and the biological material extraction carrier 1 are placed in a container and mixed, thereby associating the magnetic bead 2 with the oxide powder 3 through the nucleic acid 9 and obtaining the associated body 4. In the elution step S110, the biological material extraction carrier 1 that forms the associated body 4 is brought into contact with an elution liquid to elute the nucleic acid 9 in the elution liquid, and thereafter, the elution liquid containing the nucleic acid 9 is discharged from the container in a state where the biological material extraction carrier 1 is fixed to the inner wall of the container by applying an external magnetic field thereto.

In such a biological material extraction method, in the elution liquid containing the nucleic acid 9, the associated body 4 in which the magnetic bead 2 and a plurality of particles of the oxide powder 3 are associated through the nucleic acid 9 (biological material) is formed. Such an associated body 4 contains a plurality of particles of the oxide powder 3, and therefore has a large specific surface area and adsorbs a large amount of the nucleic acid 9. On the other hand, the associated body 4 contains the magnetic bead 2, and therefore, even if it contains the oxide powder 3 having no magnetism, it can be captured by an external magnetic field, and therefore, magnetic separation is possible. Then, in the associated body 4, a plurality of particles of the oxide powder 3 smaller than the magnetic bead 2 are contained, and therefore, even if the size of the magnetic bead 2 is increased, a decrease in the specific surface area can be suppressed. Therefore, the magnetic bead 2 having a large particle diameter and a high saturation magnetization can be used, and the magnetic attractive force of the associated body 4 can be increased. As a result, according to the biological material extraction method, the nucleic acid 9 can be extracted and recovered in high yield while increasing the separation speed in magnetic separation.

In addition, the oxide powder 3 enters a gap between the magnetic beads 2 so as to reduce the gap, and therefore, the amount of a liquid remaining in the gap (residual liquid amount) after magnetic separation can be reduced.

Further, the elution liquid containing the nucleic acid 9 (biological material) obtained in the elution step S110 contains the oxide powder 3. The elution step S110 includes an operation of separating the oxide powder 3 from the elution liquid by performing a centrifugation treatment for the elution liquid containing the nucleic acid 9 and the oxide powder 3.

This can prevent the oxide powder 3 from being subjected to a test together with the nucleic acid 9.

Hereinabove, the biological material extraction carrier and the biological material extraction method according to the present disclosure have been described with reference to the embodiments illustrated in the drawings, however, the present disclosure is not limited thereto. For example, the biological material extraction carrier according to the present disclosure may be configured to add any component to the above-mentioned embodiment. Further, the biological material extraction method according to the present disclosure may be configured to add any desired step to the above-mentioned embodiment.

EXAMPLES

Next, specific Examples of the present disclosure will be described.

5. Production of Biological Material Extraction Carrier

5.1. Example 1

First, a magnetic metal powder having an alloy composition represented by the composition formula $Fe_{73}Si_{11}Cr_2B_{11}C_3$ was produced by a high-pressure water atomization method. The numbers in the compositional formula represent the content (at %) of each element. The metal structure analysis of the obtained powder was performed by X-ray diffractometry, and it was confirmed that the main structure is an amorphous structure.

Thereafter, silicon oxide ($SiO_2$) was deposited on the particle surface of the magnetic metal powder by the Stober method, thereby obtaining a magnetic bead. In the Stober method, first, 100 g of the magnetic metal powder was dispersed in 950 mL of ethanol and mixed, and this mixed liquid was stirred for 20 minutes by an ultrasonic wave applicator. After stirring, a mixed solution of 30 mL of pure water and 180 mL of aqueous ammonia was added thereto, and the mixture was further stirred for 10 minutes. Thereafter, a mixed liquid of tetraethoxysilane (TEOS) and 100 mL of ethanol was further added thereto, followed by stirring, thereby forming a silicon oxide film on the particle surface of the magnetic metal powder. Thereafter, the obtained silicon oxide film was washed with ethanol and acetone, respectively. After washing, the film was dried at 65° C. for 30 minutes and further heated at 200° C. for 90 minutes. Thereby, the magnetic bead was obtained.

With respect to the obtained magnetic bead, the average particle diameter was measured by a laser diffraction method. The measurement results are shown in Table 1.

In addition, a silicon oxide powder (fumed silica) was prepared as an oxide powder.

With respect to the prepared silicon oxide powder, the average particle diameter was measured. The measurement results are shown in Table 1.

In addition, as a particle diameter ratio, the ratio of the average particle diameter d3 of the oxide powder 3 to the average particle diameter d2 of the magnetic bead 2 (d3/d2) was calculated. Further, as a volume ratio, the ratio of the volume v3 of the oxide powder 3 to the volume v2 of the magnetic bead 2 (v3/v2) was calculated. The calculation results are shown in Table 1.

Then, the produced magnetic bead and the prepared oxide powder were mixed, thereby obtaining a biological material extraction carrier.

5.2. Examples 2 to 6 and Comparative Examples 1 to 7

Biological material extraction carriers were obtained in the same manner as in Example 1 except that the average particle diameter d2 of the magnetic bead and the average particle diameter d3 of the oxide powder were changed so that the particle diameter ratio became the value shown in Table 1, and the used amount of the magnetic bead and the used amount of the oxide powder were changed so that the volume ratio became the value shown in Table 1.

5.3. Examples 7 to 12 and Comparative Examples 8 to 11

Biological material extraction carriers were obtained in the same manner as in Example 1 except that the average particle diameter d2 of the magnetic bead and the average particle diameter d3 of the oxide powder were changed so that the particle diameter ratio became the value shown in Table 2, and the used amount of the magnetic bead and the used amount of the oxide powder were changed so that the volume ratio became the value shown in Table 2.

6. Evaluation of Biological Material Extraction Carrier

6.1. Evaluation of Yield of Nucleic Acid

First, salmon sperm-derived DNA was prepared as a nucleic acid model, and lysozyme was prepared as a contaminant model.

Subsequently, each of the biological material extraction carriers of respective Examples and Comparative Examples was dispersed in pure water and stirred, thereby preparing an extraction carrier suspension. Hereinafter, the biological material extraction carrier is also abbreviated as "extraction carrier". The content of the extraction carrier in the extraction carrier suspension was set to 53.17 mass %.

Subsequently, the reagents other than the nucleic acid were left to reach room temperature, and then, the reagents were added to a tube in the following order.

10 μL of pure water
75 μL of 0.1 μg/μL nucleic acid dispersion
750 μL of dissolution/adsorption liquid
15 μL of 10 μg/μL lysozyme aqueous solution
40 μL of extraction carrier suspension Subsequently, the contents of the tube were stirred with a vortex mixer for 10 minutes, and thereafter, the tube was placed on a magnetic stand and left for 30 seconds. After the extraction carrier was magnetically collected, the supernatant was removed.

Subsequently, 900 μL of a washing liquid was added to the tube, and the mixture was stirred with a vortex mixer for 5 seconds, and then centrifuged. Thereafter, the tube was placed on a magnetic stand and left for 30 seconds. After the extraction carrier was magnetically collected, the supernatant was removed. Thereafter, addition of the washing liquid, magnetic collection, and removal of the supernatant were performed again.

Subsequently, 900 μL of a 70% ethanol aqueous solution was added to the tube, and the mixture was stirred with a vortex mixer for 5 seconds, and then centrifuged. Thereafter, an operation of pipetting the contents of the tube up and down was performed once. Then, the tube was placed on a magnetic stand and left for 30 seconds. After the extraction carrier was magnetically collected, the supernatant was removed. Thereafter, addition of the ethanol aqueous solution, magnetic collection, and removal of the supernatant were performed again. Subsequently, the tube was centrifuged, and the remaining supernatant was removed.

Subsequently, 100 μL of pure water was added to the tube, and then, the mixture was stirred with a vortex mixer for 10 minutes, thereby eluting the nucleic acid. Thereafter, the tube was placed on a magnetic stand and left for 30 seconds. After the magnetic bead was magnetically collected, the elution liquid containing the nucleic acid and the oxide powder was recovered in another tube.

Subsequently, the tube containing the nucleic acid and the oxide powder was centrifuged for 10 minutes. The maximum centrifugal force in the centrifugation was set to 50,000 g. Thereby, the oxide powder was precipitated. Then, the elution liquid containing the nucleic acid was recovered in another tube.

Subsequently, the recovered elution liquid was placed in an absorptiometer, and the concentration of the nucleic acid in the elution liquid was quantitatively determined from the absorbance at a wavelength of 260 nm. Then, the recovered amount of the nucleic acid was calculated from the determined concentration, and the ratio of the recovered amount of the nucleic acid to the input amount of the nucleic acid was calculated as the yield of the nucleic acid. Since a nucleic acid base has an absorption maximum near 260 nm, the absorbance at a wavelength of 260 nm is used for quantitative determination of the concentration of the nucleic acid. Then, the calculated yield of the nucleic acid was evaluated in light of the following evaluation criteria.

A: The yield of the nucleic acid is 80% or more.
B: The yield of the nucleic acid is 60% or more and less than 80%.
C: The yield of the nucleic acid is 40% or more and less than 60%.
D: The yield of the nucleic acid is less than 40%.

The evaluation results are shown in Tables 1 and 2.

6.2. Evaluation of Magnetic Separation Speed

First, each of the biological material extraction carriers of respective Examples and Comparative Examples was dispersed in water, thereby preparing an extraction carrier dispersion. The obtained extraction carrier dispersion was placed in a spectroscopic cell and stirred with a vortex mixer for 10 minutes, and then, the cell was placed in a spectrophotometer. Thereafter, the measurement wavelength was set to 550 nm, and the measurement of absorbance was started.

After starting the measurement, a permanent magnet was brought into close contact with the side of the spectroscopic cell. Then, a time from that point until the absorbance value reached 10% of the initial value was measured. This time can be regarded as a time required for completing magnetic separation (magnetic separation time).

Subsequently, a magnetic separation speed was evaluated by comparing the magnetic separation time with the following evaluation criteria.

A: The magnetic separation time is less than 20 seconds.
B: The magnetic separation time is 20 seconds or more and less than 40 seconds.
C: The magnetic separation time is 40 seconds or more and less than 60 seconds.
D: The magnetic separation time is 60 seconds or more.

The evaluation results are shown in Tables 1 and 2.

6.3. Evaluation of Residual Liquid Amount

First, the weight of an empty tube was measured. The measurement result is represented by "weight a".

Subsequently, an extraction carrier dispersion in which the extraction carrier content was set to 38.5 mass % was stirred with a vortex mixer, thereby preparing an extraction carrier suspension. Subsequently, a 40 μL portion was withdrawn from the extraction carrier suspension and placed in the tube whose weight was measured. Then, the weight of the tube was measured. The measurement result is represented by "weight b".

Subsequently, 900 μL of a 70% ethanol aqueous solution was dispensed into the tube, and the mixture was stirred with a vortex mixer for 5 seconds. Thereafter, the tube was placed on a magnetic stand and left for 30 seconds. After the extraction carrier was magnetically collected, the supernatant was recovered with a micropipette. The weight of the tube after recovering the supernatant was measured. The measurement result is represented by "weight c".

Subsequently, a residual liquid amount was calculated from the weight a, the weight b, and the weight c. Then, the calculated residual liquid amount was evaluated in light of the following evaluation criteria.

A: The residual liquid amount is less than 30 μL.

B: The residual liquid amount is 30 μL or more and less than 50 μL.

C: The residual liquid amount is 50 μL or more and less than 70 μL.

D: The residual liquid amount is 70 μL or more.

The evaluation results are shown in Tables 1 and 2.

TABLE 1

| | | | Example 1 | Example 2 | Example 3 | Example 4 | Example 5 | Example 6 | Comparative Example 1 |
|---|---|---|---|---|---|---|---|---|---|
| Magnetic bead | Average particle diameter d2 | μm | 5 | 5 | 0.5 | 0.5 | 50 | 50 | 0.1 |
| | Used emount | mg | 40 | 40 | 40 | 40 | 40 | 40 | 40 |
| Oxide powder | Average particle diameter d3 | μm | 0.2 | 0.0.5 | 0.02 | 0.2 | 0.1 | 0.5 | 0.05 |
| | Used amount | mg | 2 | 2 | 2 | 2 | 2 | 2 | 2 |
| Combination of magnetic bead and oxide powder | Particle diameter ratio [d3/d2) | % | 4.0 | 1.0 | 4.0 | 40.0 | 0.2 | 1.0 | 50.0 |
| | Volume ratio (v3/v2) | % | 17.5 | 17.5 | 17.5 | 17.5 | 17.5 | 17.5 | 17.5 |
| Evaluation results of biological material extraction carrier | Yield of nucleic acid | — | A | A | A | A | B | B | B |
| | Magnetic separation speed | — | A | A | B | B | A | A | D |
| | Residual liquid amount | — | A | A | A | A | B | B | A |

| | | Comparative Example 2 | Comparative Example 3 | Comparative Exemple 4 | Comparative Example 5 | Comparative Example 6 | Comparative Example 7 |
|---|---|---|---|---|---|---|---|
| Magnetic bead | Average particle diameter d2 | 100 | 5 | 50 | 0.1 | 5 | 50 |
| | Used emount | 40 | 40 | 40 | 40 | 40 | 40 |
| Oxide powder | Average particle diameter d3 | 0.04 | 2.5 | 0.02 | — | — | — |
| | Used amount | 2 | 2 | 2 | — | — | — |
| Combination of magnetic bead and oxide powder | Particle diameter ratio [d3/d2) | 0.04 | 50.0 | 0.04 | — | — | — |
| | Volume ratio (v3/v2) | 17.5 | 17.5 | 17.5 | — | — | — |
| Evaluation results of biological material extraction carrier | Yield of nucleic acid | D | D | C | A | C | C |
| | Magnetic separation speed | A | A | A | D | A | A |
| | Residual liquid amount | D | B | C | B | B | C |

TABLE 2

| | | | Example 7 | Example 8 | Example 9 | Example 10 | Example 11 |
|---|---|---|---|---|---|---|---|
| Magnetic bead | Average particle diameter d2 | μm | 5 | 5 | 5 | 5 | 5 |
| | Used amount | mg | 40 | 80 | 20 | 200 | 80 |
| Oxide powder | Average particle diameter d3 | μm | 0.2 | 0.2 | 0.2 | 0.2 | 0.2 |
| | Used amount | | 2 | 2 | 2 | 2 | 0.05 |
| Combination of magnetic bead and oxide powder | Particle diameter ratio (d3/d2) | % | 4.0 | 4.0 | 4.0 | 4.0 | 4.0 |
| | Volume ratio (v3/v2) | % | 17.5 | 8.8 | 35.0 | 3.5 | 0.2 |

TABLE 2-continued

| | | | | | | | |
|---|---|---|---|---|---|---|---|
| Evaluation results of biological material extraction carrier | Yield of nucleic acid | — | A | A | B | A | B |
| | Magnetic separation speed | — | A | A | B | B | A |
| | Residual liquid amount | — | Å | A | A | B | B |
| | | | Example 12 | Comparative Example 8 | Comparative Example 9 | Comparative Example 10 | Comparative Example 11 |
| | Magnetic bead | Average particle diameter d2 | 5 | 5 | 5 | 5 | 4 |
| | | Used amount | 40 | 15 | 300 | 80 | 40 |
| | Oxide powder | Average particle diameter d3 | 0.2 | 0.2 | 0.2 | 0.2 | 0.2 |
| | | Used amount | 4 | 3 | 0.05 | 0.01 | 5 |
| | Combination of magnetic bead and oxide powder | Particle diameter ratio (d3/d2) | 4.0 | 4.0 | 4.0 | 4.0 | 4.0 |
| | | Volume ratio (v3/v2) | 35.0 | 70.0 | 0.06 | 0.04 | 52.5 |
| | Evaluation results of biological material extraction carrier | Yield of nucleic acid | B | D | C | D | D |
| | | Magnetic separation speed | A | A | B | A | A |
| | | Residual liquid amount | B | A | D | C | D |

As is clear from Tables 1 and 2, it was confirmed that the biological material extraction carrier of each Example has a high separation speed in magnetic separation and can extract a biological material in high yield. It was also found that the biological material extraction carrier of each Example can suppress the residual liquid amount small.

What is claimed is:

1. A biological material extraction carrier, comprising:

a magnetic bead including a magnetic metal powder and a first coating layer that coats a particle surface of the magnetic metal powder and that is made of a first oxide material; and an oxide powder, in which a particle surface is made of a second oxide material, and an average particle diameter is smaller than that of the magnetic bead, wherein a particle of the oxide powder has a core portion, and a second coating layer that coats a surface of the core portion and that is made of the second oxide material, and wherein the core portion is formed of a material selected from the group consisting of a resin material, a carbon material, and a glass material.

2. The biological material extraction carrier according to claim 1, wherein the average particle diameter of the magnetic bead is 0.5 μm or more and 50 μm or less.

3. The biological material extraction carrier according to claim 1, wherein the average particle diameter of the oxide powder is 0.1% or more and 40.0% or less of the average particle diameter of the magnetic bead.

4. The biological material extraction carrier according to claim 1, wherein a volume of the oxide powder is 0.1% or more and 40.0% or less of a volume of the magnetic bead.

5. The biological material extraction carrier according to claim 1, wherein the first oxide material contains silicon oxide.

6. The biological material extraction carrier according to claim 1, wherein the second oxide material contains silicon oxide.

* * * * *